(12) United States Patent
Vollhardt et al.

(10) Patent No.: US 6,387,398 B1
(45) Date of Patent: *May 14, 2002

(54) PROCESS FOR PRODUCING COSMETIC AND PHARMACEUTICAL FORMULATIONS, AND PRODUCTS COMPRISING SAME

(75) Inventors: Jürgen Vollhardt, Lincoln Park, NJ (US); Nisha Malkan, Nanuet; Robert P. Manzo, Goshen, both of NY (US)

(73) Assignee: Dragoco Gerberding & Co. AG (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/365,033

(22) Filed: Aug. 2, 1999

Related U.S. Application Data (63) Continuation-in-part of application No. 09/120,269, filed on Jul. 22, 1998, now Pat. No. 6,045,823.

(51) Int. Cl.⁷ ................. A61K 9/127; A61K 9/133; A61K 7/00

(52) U.S. Cl. ................. 424/450; 424/484; 424/485; 424/488; 424/489; 424/490; 424/493; 424/496; 424/499; 424/500; 424/64; 424/65; 424/401

(58) Field of Search ................. 426/450, 401, 426/484, 485, 488, 489, 490, 64, 65, 76.2, 493, 496, 499, 500

(56) References Cited

U.S. PATENT DOCUMENTS

| | | | | |
|---|---|---|---|---|
| 4,708,861 A | * | 11/1987 | Popescu | 424/1.1 |
| 4,766,046 A | * | 8/1988 | Abra | 424/450 |
| 4,906,476 A | * | 3/1990 | Radhakrishnan | 424/450 |
| 5,577,668 A | * | 11/1996 | King | 239/559 |

\* cited by examiner

*Primary Examiner*—Gollamudi S. Kishore
(74) *Attorney, Agent, or Firm*—Pendorf & Cutliff (57) ABSTRACT

Cosmetic or pharmaceutical formulations such as (a) anhydrous cosmetic stick formulations and (b) anhydrous aerosol spray formulations, comprising an organic dispersion medium having particles dispersed therein, which particles are preferably prepared by a process comprising spray-drying a mixture of liposome encapsulated active agent, modified starch, and optionally a hydrocolloid gum such as maltodextrin.

15 Claims, 1 Drawing Sheet

Bisabolol release in presence of water

PROCESS FOR PRODUCING COSMETIC AND PHARMACEUTICAL FORMULATIONS, AND PRODUCTS COMPRISING SAME

REFERENCE TO RELATED APPLICATIONS

This is a continuation-in-part of application Ser. No. 09/120,269 filed Jul. 22, 1998, entitled "PROCESS FOR PRODUCING SOLID ANHYDROUS COMPOSITION, AND PHARMACEUTICAL AND COSMETIC PRODUCTS COMPRISING SAME", now U.S. Pat. No. 6,045,823.

BACKGROUND OF THE INVENTION

1. Field of the Invention

The invention relates to cosmetic and pharmaceutical formulations such as (a) stick formulations and (b) formulations comprising a liquid dispersion medium.

In particular the invention relates to:

(a) essentially anhydrous cosmetic stick formulations such as lip balms, lipsticks, and underarm deodorant or antiperspirant sticks, and (b) essentially anhydrous formulations comprising a liquid dispersion medium, e.g. anhydrous aerosol spray formulations such as deodorant, antiperspirant or perfume sprays.

Application of a topical biological active agent directly to skin results in an initial burst of activity. However, this activity phases out quickly. Accordingly, to prolong or delay activity, the active agent must be formulated into a product which gradually releases active agent. It is even more preferred to formulate the product in such a manner that the active agent is released precisely at the time of greatest need. Consumers expect a high level of sophistication in their products. There is thus a need for an intelligent skin care product which can provide not only prolonged release of active agent, but which also coordinates peak delivery of active agent to a particular biological demand. This responsive delivery is referred to herein as controlled delivery.

2. Description of the Related Art

In recent years increasing attention has been paid to the development of liposomes for use as microscopic "containers". Liposomes have been used to deliver active agent to the skin. For example, U.S. Pat. No. 5,128,139 (Brown et al.) teaches a deodorant comprising liposomes containing grapefruit seed extract. The bioactive agents are entrapped within multilamellar liposomes complexes to provide release over time. Brown et al. acknowledge that liposomes are inherently unstable and tend to break apart, releasing the contents within. Brown et al. thus layers the liposomes or forms them into clusters such that the liposomes which are confined within or are sandwiched between outer layers of liposomes are protected and are more likely to remain stable, while the outer "sacrificial" liposomes tend to break apart releasing their contents during product formulation. This premature release of liposome content is undesirable where the liposome content is a high-value or potent active agent. Further, this formulation does not provide controlled release, i.e., co-ordination of release in response to biologic demand. U.S. Pat. No. 4,937,078 to Mezie et. al. discloses the incorporation of topical anesthetic active agents into liposomes which essentially encapsulate the active ingredient within layers of lipid material. It is reported that these lipid vesicles provide a more pronounced cutaneous anesthetic or analgesic effect while employing less of the topical anesthetic agent. The lipid vesicles allegedly provide a means of prolonging the permeation rate without the risk for discomfort due to numbness or systemic reactions. However, prolonging release simply refers to constant rate of release over an extended period of time. There is no mention of suppressing active agent until triggered by a biologic need, then releasing an amount of active agent commensurate with the need.

U.S. Pat. No. 5,510,120 (Jones, et al.) teaches a cosmetic composition for topical application to the skin and/or hair. The composition comprises microcapsules or liposomes which enclose a cosmetically-effective benefit agent (e.g., an agent intended to modify or enhance body odor) active at a target location accessible by application to the skin and/or hair. The particles have means, namely lectin, for binding to targeted microorganisms present on the skin and/or hair, for example those bacteria responsible for skin disorders, scalp irritation, and underarm and foot odor. The encapsulated active agent may be used in combination with a vehicle or carrier such as water, various liquid substances, and various powders such as chalk, talc, fullers earth, kaolin, starch, gums, colloidal silica, etc. While Jones et al. teach targeting delivery of active agent in terms of location, they do little to target delivery in terms of time, i.e., controlling release to peak at the time of greatest need.

U.S. Pat. No. 5,783,211 (Manzo et al) describes the production of starch based particles which encapsulate active agents such as pharmaceutical or cosmetic active ingredients and provide controlled release of these active agents. The material produced according to this patent is a powdery cosmetic formulation, e.g., baby powder. As the starch absorbs moisture, the liposomes disintegrate resulting in the release of the active agent. The particles thus provide controlled release of the encapsulated active agent precisely at the time of need. Unfortunately, dry powder formulations are not suitable for use by most adults, since fine white powders do not remain on the skin and tend to migrate through clothes and show up particularly on the outside surface of dark clothes.

It would thus be of interest to be able to adapt the moisture triggered controlled release system of U.S. Pat. No. 5,783,211 to other cosmetic applications. However, liposomes are delicate, and it would be expected that active-agent containing liposomes would be destroyed during the process of formulating cosmetic stick products or aerosol spray products. Further, it would be expected that waxes and oleophilic organic ingredients of stick formulations and organic dispersion media (propellants) used in aerosol sprays would mask the liposomes, and interfere with the controlled release of active substance in response to biological demand.

Accordingly, there remains a need for a new type of delivery system which satisfies a number of requirements, namely, it must be capable of formulating even labile compounds, it must provide enhanced stability, it must be aesthetically pleasing, it must increase efficacy, and it must have reduced irritancy, it must remain in place, and most importantly, it must remain capable of releasing active ingredient in response to biological demand.

SUMMARY OF THE INVENTION

It is an object of the present invention to provide a pharmaceutical and/or cosmetic delivery system which provides controlled release of active agent, such as a bacteriostat, an anti-inflammatory agent, a fragrance, or a dye (e.g., a dye which changes color in reaction to change in pH, upon exposure to moisture, exposure to light, etc.).

Another objective of this invention is to provide a formulation which can be applied to skin and which remains on the skin.

Another objective of this invention is to provide a pharmaceutical and/or cosmetic delivery system in which diverse active ingredients such as Dragosantol and Farnesolm can be insulated from each other and other ingredients, and be protected from degradative processes such as oxidation.

It has now surprisingly been found that the dry powders formed in accordance with U.S. Pat. No. 5,783,211, though sensitive enough to decompose upon exposure to body moisture, are nevertheless sufficiently stable such that the particles stay enriched in active ingredient content during the process of manufacturing and storage of dry stick anhydrous cosmetic preparations and aerosol spray formulations.

Correspondingly, the invention provides a (preferably anhydrous) cosmetic or pharmaceutical product (formulation) comprising:

a solid or liquid dispersion medium, and about 0.01–20 weight percent, based upon the total weight of said product, of particles dispersed in said dispersion medium, said particles comprising modified starch, liposomes containing biologically active agent, and, optionally, a hydrocolloid gum.

Typically, said particles have an average particle size in the range of 20–120 μm.

Preferably said liposomes have a droplet size of from 100 to 1000 nm, more preferably from 200 to 300 nm.

Although anhydrous products (formulations) are always preferred, a water content of up to 5% by weight is acceptable in certain applications, in particular in solid cosmetic products.

A product according to the invention can be a cosmetic product wherein the dispersion medium is a solid lipophilic organic matrix comprising

10–55 wt. % volatile oil,

1–35 wt. % liquid emollient, and

12–30 wt. % low melting point wax.

Such a product is preferred, as far as solid cosmetic formulations are concerned.

Said volatile oil can advantageously be a cyclic or linear polydimethylsiloxane containing between 3–9 silicon atoms or a linear polydimethylsiloxane illustrated by the formula:

$$(CH_3)_3Si-O[Si(CH_3)_2-O]_n-Si(CH_3)_3$$

where n is an integer with a value of about 1–7.

Additionally or alternatively, the volatile oil ingredient can comprise a $C_{12}-C_{20}$ branched-chain hydrocarbon.

The liquid emollient ingredient is preferably a water-insoluble organic acid, ester or ether compound.

The wax ingredient is advantageously selected from $C_8-C_{30}$ alcohol, acid, ester and amide compounds.

The hydrocolloid gum optionally present in the product according to the present invention is preferably selected from the group consisting of xanthan, maltodextrin, galactomanan and tragacanth, maltodextrin being preferred.

The biologically active agent encapsulated in said liposomes can be selected from the group consisting of anti-inflammatory, antiphlogistic, antibacterial, anti-perspirant, astringent, and anti-fungal agents. In particular, the biologically active agent can be selected from the group consisting of bisabolol, tocopherol and farnesol.

Within the concept of the present invention cosmetic or pharmaceutical products are advantageously formed by a process comprising (a) incorporating a biologically active agent into liposomes (b) forming an aqueous mixture of active agent encapsulating liposomes, starch and, optionally, a hydrocolloid gum, (c) spray drying said mixture to form a dry powder composition, (d) dispersing said dry powder composition into a (preferably anhydrous) dispersion medium.

The dispersion obtained after step (d) can be further processed to give a cosmetic or pharmaceutical product. In step (d) the dispersion medium is chosen according to the desired properties of the product.

A solid cosmetic or pharmaceutical (preferably anhydrous) product is favourably formed by a process comprising steps (a)–(c) as above, (d) dispersing said dry powder composition into a solid (preferably anhydrous) lipophilic cosmetic matrix, and (e) shaping the product of step (d).

A cosmetic or pharmaceutical anhydrous aerosole spray formulation is advantageously formed by a process comprising steps (a)–(c) as above, and (d) dispersing said dry powder composition into a (typically anhydrous) liquid dispersion medium.

If more than 50% of the small amount of water sometimes present in the cosmetic or pharmaceutical products according to the invention has already been present in the dry powder composition after spray drying (step (c)), the obtained product is considered to be "essentially anhydrous". Within the concept of the present invention, essentially anhydrous cosmetic or pharmaceutical products are preferred as the dry powder composition (comprising the liposomes containing biologically active agent) within the product remains intact for a long time only in an essentially water-free environment.

The present invention utilizes the moisture triggered release technology of U.S. Pat. No. 5,783,211 (Manzo et al.), preferably for lipophilic active ingredients, and does this by incorporating these particles in an anhydrous (or nearly anhydrous) organic matrix.

More specifically, the objects of the invention are achieved by encapsulating active agents in liposomes, preferably nanosomes having an average diameter of approximately 200 nm, which are then mixed and spray dried with a carrier or matrix forming composition, preferably a water absorptive composition such as modified starch and preferably also maltodextrin, followed by incorporation of the resulting particles (dry powder) in an organic dispersion medium (solid or liquid) and (a) if the dispersion medium is solid (i.e. a matrix), forming the composition into a cosmetic stick such as a lip balm, an underarm deodorant stick or a lipstick, or (b) if the dispersion medium is liquid, dispersing the particles into the liquid dispersion medium. Liposomes act as the delivery agents for active agents such as Dragosantol®, Farnesol™, antiherpetically active substances, etc. As the water absorbent component of the particles according to the present invention absorbs water, it acts as a trigger on the intimately associated liposome component, triggering a loss of structural integrity in the liposome carrier followed by the release of the active agent. Thus, in response to a condition such as perspiration, the particles in the cosmetic stick according to the present invention release one or more of, e.g., an anti-perspirant, anti-microbial, cooling, tingling, anti-inflammatory agent, fragrance or dye (e.g., a dye which changes color in reaction to change in pH, upon exposure to moisture, exposure to light, etc.).

Within the concept of the present invention, cosmetic stick formulations could be solid (including semisolid) but anhydrous formulations as they are used to make, e.g., chap sticks, lipsticks or non-aqueous deodorant sticks.

Within the concept of the present invention, aerosol spray formulations can be anhydrous dispersions, suspensions or slurries, which have to be shaken before use. A liquid dispersion medium used within the concept of the invention, for example in an aerosol spray formulation, should be an (essentially) anhydrous liquid lipophilic medium (such as a propellant) and/or is preferably selected from the group consisting of (a) hydrocarbons, (b) fluorocarbons, (c) dimethylether, and (d) mixtures thereof.

By incorporating a moisture triggered release system as described in U.S. Pat. No. 5,783,211 into a cosmetic stick formulation or aerosol spray formulation a release of an active product could be achieved at a certain point during the application process. Not only is a prolongation of activity caused, but also a maximization, because the active agent will be held back for a longer period of time and released for peak activity in response to demand when it is ultimately needed. The active agent will not be wasted when not needed, and will be available to provide activity when needed and will last longer.

For example, a deodorizing agent could be released after application of a non-aqueous deodorant stick or aerosol spray when the person begins to sweat. This is the point when most activity is needed. Other possible activities might be: generation of a fragrance; release of a sensory stimulant such as releasing menthol to provide a cool sensation, releasing jambu (jambu oleoresin, an extract from *Spilanthes acmella*) to provide a tingling sensation, for example, on the lips in response to kissing, or otherwise generating a physiological skin activity; or providing a change or an enhancement in color intensity in, e.g., a lipstick, by timed release of dyes.

The foregoing has outlined rather broadly the more pertinent and important features of the present invention in order that the detailed description of the invention that follows may be better understood and so that the present contribution to the art can be more fully appreciated. Additional features of the invention will be described hereinafter. It should be appreciated by those skilled in the art that the conception and the specific embodiments disclosed may be readily utilized as a basis for modifying or designing other biologically active agent delivery systems for carrying out the same purposes of the present invention. It should also be realized by those skilled in the art that such equivalent structures and the processes for forming them do not depart from the spirit and scope of the invention as set forth in the appended claims.

BRIEF DESCRIPTION OF THE DRAWINGS

For a fuller understanding of the nature and objects of the present invention reference should be made by the following detailed description taken in with the accompanying drawings in which.

Some substances of major relevance within the concept of the invention are hereafter discussed in detail:

DETAILED DESCRIPTION OF THE INVENTION

1. Liposome Encapsulated Active Agent Particles

Techniques for the formation of liposome encapsulated active agent, and techniques for forming starch based particles having these liposomes incorporated therein, are described in great detail in U.S. Pat. No. 5,783,211 (Manzo et al.) and the publication WO 98/11877, the entirety of which is incorporated herein by reference. These particles, sometimes referred to as Starchosomes®, form the active particle phase of the cosmetic or pharmaceutical products of the present invention.

Preparation of liposomes and incorporation of active agent in liposomes is well known and reference may be made to a variety of patents and treatises. For example, liposomes or lipidic particles can be prepared in accordance with U.S. Pat. No. 5,783,211 (Manzo et al.), PCT publication WO 98/11877 or U.S. Pat. No. 5,077,057 (Szoka, Jr.), or can be formed from nonphosphal lipid components which have the potential to form lipid bilayers is disclosed in Biochim. Biophys. Acta., 19:227–232 [1982], the disclosures of which are incorporated herein by reference. A general discussion of techniques for preparation of liposomes and of medication encapsulating liposomes can be found in U.S. Pat. No. 4,224,179 (Schneider). Further examples of liposome encapsulation techniques and products can be found in U.S. Pat. No. 5,356,633 (Woodle, et al.); U.S. Pat. No. 5,376,380 (Kikuchi, et al.); U.S. Pat. Nos. 5,446,070, 5,332,576 and 5,234,957 (Mantelle); U.S. Pat. No. 5,447,930 (Nayak); U.S. Pat. No. 5,470,579 (Bonte, et al.); U.S. Pat. No. 5,476,852 (Cauwenbergh); U.S. Pat. No. 5,514,374 (Bonte, et al.); U.S. Pat. No. 5,514,712 (LeClere); U.S. Pat. No. 5,519,020 (Smith, et al.); U.S. Pat. No. 5,476,651 (Meybeck, et al.); U.S. Pat. No. 5,034,228 (Meybeck, et al.); U.S. Pat. No. 4,942,038 (Wallach); U.S. Pat. No. 5,188,837 (Domb); U.S. Pat. No. 4,946,683 (Forssen); U.S. Pat. No. 5,169,631 (Rase et al.); U.S. Pat. No. 5,137,725 (Handjani et al.); Ann. Rev. Biophys. Bioeng. 9:467 (1980); U.S. Pat. No. 4,235,871, incorporated herein by reference. The preparation of multilamellar vesicles (MLVs) by thin-film processing U.S. Pat. No. 4,737,923, incorporated by reference.

In a preferred embodiment of the present invention the particles are formed by a process wherein active substance is mixed with lecithin to form liposomes (actually nanosomes, 200 nm in size) under action of a high pressure high shear force homogenizer. At this stage the product looks like milk, and a carrier substance, namely a blend of maltodextrin (a polysaccharide between dextrin and maltose) and modified (in particular encymatically degradated) starch, is mixed in under low shear force mixing. Before spray drying the pH-value could be adjusted to about 5.0. The mixture is spray dried to form irregular, off-white particles.

The delivery system of the present invention can be variously formulated so long as the product comprises active agent at least partially encapsulated in liposomes, which liposomes are in turn physically or chemically adsorbed onto or dispersed within a dry powder carrier or matrix to form dry particles in such a way that the dry powder carrier or matrix protects and stabilizes the liposomes while dry, and that absorption of water by the dry powder triggers release of active agent from the liposome.

One specific example of a dry powder composition for incorporation into the anhydrous solid or liquid dispersion medium according to the present invention is a powder which contains bisabolol (the main ingredient in a composition available under the tradename Dragosantol® from Dragoco Corporation, Totowa, N.J.) as the active ingredient. Bisabolol is known to have antiphlogistic properties, and is generally applied to the skin in the form of a solution or in form of emulsion systems. In accordance with the present invention bisabolol is incorporated in liposomes, and the liposomes are mixed with a starch-based carrier system and spray dried to form Starchosomes® wherein the conventional aqueous phase of liposome is up to more than 95% removed and replaced with a starch-based carrier system. The carrier (i.e., modified starch and maltodextrin) is a moisture absorbent which, upon absorbing moisture, triggers the mechanism for the elution of the Bisabolol onto the skin. So long as the powder remains dry (virtually free of water), the liposomes remain stable and active ingredient is preserved. As the powder absorbs increasing amounts of moisture, increasing amounts of active agent are released. This relationship provides a stable, long lasting, controlled anti-inflammatory property.

While liposomes, especially those prepared from lecithin, are preferable for the purposes of carrying out the present invention, micelles encapsulating active agents may be prepared from various non-polar materials in accordance with standard practices known to those skilled in the art of emulsion chemistry. Such micelles may be formed from naturally occurring oils, fats, or the like.

The formulation according to the present invention is in no way limited to bisabolol, and can be used to provide controlled delivery of an extensive array of pharmaceutically or biologically active agents.

Another specific example of a suitable controlled release substance is farnesol (3,7,11-trimethyl-dodeca-2,6,10-triene-1-ol). As taught in U.S. Pat. No. 4,220,665 (Klein), farnesol is highly effective in inhibiting growth of odor forming bacterial flora of the skin at relatively low concentrations.

Other suitable active agents include anti-perspirant, astringents, anti-inflammatory, anti-microbial, anti-fungal, etc. agents as well known in the art. It is not necessary that all active ingredient present in the final product be encapsulated in the liposomes. Some free active agent may be added to give some immediate action effect.

The various active agents which can be incorporated in the liposomes or cosmetic products according to the present invention are too numerous to list. See, for example, U.S. Pat. No. 5,446,070 (Mantelle) which teaches topical administration of pharmaceutically active agents, which agents may be microencapsulated. Mantelle provides at columns 23–41 a very extensive list of anesthetic type drugs which may be microencapsulated with liposomes. These anesthetic type drugs are only one class of active agent which can be formulated into the present invention.

An active agent which can provide a tingling sensation, which may make lipstick more interesting, particularly to the recipient of oral contact, is jambu (jambu oleoresin, an extract from *Spilanthes acmella*). Jambu is a plant extract, identified by CAS Nr. 90131-24-1, FEMA Nr. 3783, and EINECS Nr. 290-335-0. It is commercially available as a viscous liquid, dark brown, comprising 15–20% ethanol, 15–17% spilanthol (HPLC), with a flash point of 24° C., from Robertet S. A., Grasse, Codex, France. It has a tongue tingling effect at 50 to 100 ppm.

An active agent used to impart a feeling and freshness to skin is menthol and its derivatives, e.g., commercially available as Frescolat® ML (oil soilble solid, faint odor, CAS No. 59259-38-0, INCI name: menthyl lactate) and Frescolat® MGA (colorless liquid, CAS No. 63187-91-7, INCI name: methone glycerin acetal).

A fragrance may be added to the liposome composition, the powder composition, or the cosmetic dispersion medium (liquid or solid). When fragrance is added during the formation of liposomes, the liposomes entrap the fragrance, and the fragrance is subject to periodic or controlled release. As a result, the fragrance will last longer than unencapsulated fragrance. The fragrance may be a highly volatile fragrance or a relatively inert fragrance. In the case that fragrance is encapsulated in liposome, it is preferred that the fragrance remain encapsulated and inert so long as the liposome and dry powder remain dry, and is released as the liposome is exposed to moisture.

The amount of fragrance included in the composition may vary, but a preferred amount of fragrance is about 5–40 wt. % of the spray dried particles, or about 0.5% to about 3% of the final cosmetic stick or aerosol spray composition. Quantities of fragrance outside of this preferred range may also be used, as well as significantly larger amounts, depending upon the potency and dwell time of the fragrance.

A wide variety of chemicals are known for perfumery, such as aldehydes, ketones, esters, alcohols, terpenes, and the like. A scented oil can have a light floral fragrance, such as rose extract or violet extract, or a fruity odor, such as lime, lemon or orange, or may have an artificial fragrance such as geraniol, geranyl acetate, eugenol, isoeugenol, linalool, linalyl acetate, phenethyl alcohol, methyl ethyl ketone, methylionone, isobornyl acetate, and the like.

Powders which may be used in the present invention as further carrier or matrix for the liposomes may be any powders having an ability to absorb moisture. The powders may be selected from chalk, talc, fullers earth, kaolin, starch, gums, colloidal silicon dioxide, sodium polyacrylate, tetra alkyl and/or trialkyl aryl ammonium smectites, chemically modified magnesium aluminum silicate, organically modified montmorillonite clay, hydrated aluminum silicate, fumed silica, carboxyvinyl polymer, sodium carboxymethyl cellulose, ethylene glycol monostearate.

Powders which can be solubilized in water may be used as carriers but are preferably solubilized in water and mixed with liposome to form a protective matrix around the liposomes prior to spray drying. Such soluble powder materials include gums, proteins, protein hydrolysates, (preferably gelatin which has been hydrated and rigidified with maltodextrin), and starches.

A hydrocolloid such as xanthan, maltodextrin, galactomanan or tragacanth, preferably maltodextrin, is preferably also included in the powder forming composition. Starch, or a starch/maltodextrin mixture, is the preferred matrix or carrier for use in the present invention.

For starch preparation and encapsulation techniques, reference may be made to, e.g., U.S. Pat. No. 4,911,952 (Doane et al.) and U.S. Pat. No. 4,859,377 (Shasha et al.). Extensive discussion of starches suitable for the present invention is provided in U.S. Pat. No. 5,783,211 (Manzo et al.).

Maltodextrin is preferably added to starch and forms a hydrocolloid surface upon the spray dried particles produced in accordance with the present invention. Maltodextrin is well known in the food industry, and reference may be made to U.S. Pat. Nos. 5,039,540; 5,260,304; 5,428,150; and 5,431,951 for maltodextrin processing.

The preferred method for recovering starch particles is spray drying in a manner well known in the art, see U.S. Pat. No. No. 5,783,211 (Manzo et al.). The precise manner in which the starch, liposomes and maltodextrin associate during spray drying is not yet precisely understood and varies depending upon processing parameters.

2. Lipstick or Lip Balm Formulations

Once the liposome/starch particles have been formed, they can be incorporated into an organic matrix (solid dispersion medium) for formulation into a cosmetic stick product such as a deodorant stick or lipstick. The matrix is preferably any of the non-polar matrices, such as silicon oils, waxes, hydrocarbons, triglycerides, long chain esters, etc. or other oil based matrix.

For example, this invention provides a cosmetic deodorant product comprising an anhydrous semi-solid or solid non-polar organic matrix which contains about 0.01–20, preferably 0.1–5 weight percent, based on the total product weight, and depending upon the potency of the active agent, of the above-described liposome-encapsulated active agent particles homogeneously dispersed therein. Suitable lipstick formulations and forming processes are well known to those in the art and can be easily selected by those of ordinary skill in the art. Basically, it has been found that as the proportion of polar ingredients in the matrix are increased, the stability of the liposomes tends to be decreased. Thus, the matrix should be primarily lipophilic and, for increased liposome stability, should be reduced in hydrophilic components. Examples of patents teaching anhydrous lipstick compositions of which the organic matrices and the manufacturing processes can be easily adapted to the present invention include the following, all of which are incorporated herein by reference:

U.S. Pat. No. 5,034,216 (Baron et al.) discloses anhydrous, 3-phase powder-like cosmetic products such as lipsticks comprising ethylene/acrylate copolymers, a powder phase and an oil phase.

U.S. Pat. No. 5,039,518 (Baron et al.) discloses cosmetic stick compositions such as lipsticks comprising PVP/hexydecene copolymer, esters, phenyl trimethicone, spherical silica, bismuth oxychloride, mica, and cosmetic waxes.

U.S. Pat. No. 5,080,889 (Katada et al.) discloses mono- and diacetylglycerine compositions. Said compositions are said to have superior spreadability, smoothness, low stickiness, and feeling of moisture.

U.S. Pat. No. 5,093,111 (Baker et al.) discloses anhydrous lipstick compositions comprising waxes, oils, colorants, cetearyl isocyanate sequestearate, and isopropyl hydroxy stearate.

U.S. Pat. No. 5,108,736 (Slossman) discloses pigmented cosmetic products in cake, cream, liquid or stick form made with pigments which are dispersed by the method disclosed therein to avoid processing said pigments using water.

U.S. Pat. No. 5,505,937 (Castrogiovanni et al.) teaches cosmetic compositions, particularly lipsticks, with improved transfer resistance. The compositions comprise: (a) 1–70% volatile solvent, (b) 0.1–15% silicone resin, (c) 10–45% wax, (d) 5–50% powder, and (e) 1–30% oil.

U.S. Pat. No. 5,593,662 (Deckner et al.) teach long lasting, physically stable, moisturizing lipsticks essentially free of water, the lipsticks comprising lipophilic materials as the continuous phase, and high levels of moisturizers. These sticks maximize lip moisturization while resisting separation of the moisturizer from the body of the lipstick. More particularly, the lipstick composition comprises: (a) from about 30% to about 80% lipophilic materials; (b) from about 2% to about 20% moisturizer; (c) from about 0% to about 35% of a colorant; and (d) from about 1% to about 20% of a coupling agent.

U.S. Pat. No. 4,762,715 (Lukas et al.) teaches lipstick bases suitable as matrix for pharmaceutical preparations for the topical treatment of virus infections, especially infections caused by herpes viruses and more especially by herpesvirus hominis, for example, an antivirally active combination of a sulphatised polysaccharide or a sulphatised polymer, or salts thereof, and zinc ions in the form of dissociable zinc salts, may be obtained by combining a liquid polyethylene glycol (PEG) having a low molecular weight with solid PEG having a higher molecular weight. As PEG having a low molecular weight there come into consideration especially those having an average molecular weight of between 300 and 400, and as PEG having a higher molecular weight those having an average molecular weight of between 1000 and 4000 are preferred. Mixtures of PEG 400 and PEG 1000 with a small addition of PEG 4000 are especially suitable. Depending on the types of PEG used, the proportions of liquid PEG to solid PEG lie preferably between 15+85 and 30+70 parts. Using these PEG mixtures lipsticks are obtained that have a stable shape and in use ensure an appropriate amount is rubbed onto the lips or areas of the face to be treated.

The lipstick formulation includes dyes or pigments such as lake dyes, micas or pearls, iron oxides, titanium oxides calcium carbonates, treated pigments, and mixtures thereof. Preferred for use herein are laked dyes. Laked dyes are organic pigments produced by the interaction of an oil-soluble organic dye, a precipitant, and an absorptive inorganic substrate. The lipstick composition can contain additional ingredients known in the art for use in cosmetic compositions, such as stabilizers, preservatives, skin conditioning agents, wear extending agents, and vitamins. Skin conditioning agents are well known in the art, and are summarized in The CTFA Cosmetic Ingredient Handbook, pages 79–85, 1st Edition, 1988 incorporated herein by reference. Said skin conditioning agents include emollients, humectants, occlusives, and skin protectants. Examples of skin conditioning agents include zinc oxide, beta-glycerrhetic acid, chamomoile oil, ginkgo biloba extract, pyroglutamic acid salts or esters, sodium hyalauronate, 2-hydroxyoctanoic acid, sulfur, salacylic acid, carboyxmethyl cysteine, panthenol, vitamins A and E, lanolin, cholesterol, and mixtures thereof.

3. Deodorant or Antiperspirant Solid Formulations

Within the concept of the present invention a cosmetic stick product can be formulated as a deodorant, wherein the matrix can contain between about 0.5–25 (favourably 5–25) weight percent based upon the total product of an antiperspirant compound as an additional ingredient.

Anhydrous deodorant stick formulations are known, as disclosed in U.S. Pat. No. 4,832,945 (Osipow et al.), U.S. Pat. No. 5,380,707 (Barr et al.); U.S. Pat. No. 4,725,432 (May); U.S. Pat. No. 4,524,062 (Laba et al.); and U.S. Pat. No. 5,585,093 (Murphy)

A present invention cosmetic stick product can consist of a solid lipophilic organic matrix, and may for example comprise the following parts by weight of ingredients: volatile oil—10–55 wt. %; liquid emollient 1–35 wt. %; low melting point wax—12–30 wt. %; encapsulated powder composition according to the invention—about 0.01–20, preferably 0.1–5 wt. %, depending upon activity of active agent.

The volatile oil ingredient preferably is selected from silicone and branched-chain hydrocarbon compounds.

A volatile silicone oil ingredient in a cosmetic stick product of the present invention preferably is a cyclic or linear polydimethylsiloxane containing between about 3–9 silicon atoms.

A suitable linear polydimethylsiloxane is illustrated by the formula:

$$(CH_3)_3Si-O[Si(CH_3)_2-O]_n-Si(CH_3)_3$$

where n is an integer with a value of about 1–7.

Linear volatile silicone compounds generally have viscosities of less than about 5 centistokes at 25° C., while the cyclic type compounds have viscosities of less than about 10 centistokes.

Typical of the volatile silicone compounds that can be employed for purposes of the present invention is cyclomethicone, which is a cyclic dimethylpolysiloxane conforming to the above formula where n averages between 3–6. Dow Corning 345 Fluid (Dow Corning) is a cyclic volatile silicone which is commercially available. *CTFA Cosmetic Ingredient Dictionary,* Third Edition, (Estrin et al., Editors; The Cosmetic, Toiletry and Fragrance Association, Inc.; 1982) lists cyclic silicones on page 60, under the entry "Cyclomethicone".

A volatile hydrocarbon oil type of ingredient preferably is a $C_{12}$–$C_{20}$ branched-chain hydrocarbon compound or mixture. Suitable volatile branched-chain hydrocarbon oils include isododecane ($C_{12}$), isohexadecane ($C_{16}$), isoeicosane ($C_{20}$), and the like. These types of branched-chain hydrocarbons are marketed by Permethyl Corporation under tradenames such as Permethyl 99A, Permethyl 101A and Permethyl 102A.

The liquid emollient ingredient of an cosmetic stick product is selected from one or more water-insoluble organic compounds which are liquid at 25° C. and which contribute a combination of properties that are advantageous in an inventive cosmetic stick, such as providing a low degree of irritation and toxicity in topical applications, and providing a softening or soothing effect on surface skin tissue.

The term "water-insoluble" as employed herein refers to an emollient ingredient which has a water-solubility of less than about one gram per 100 grams of water at 25° C.

Preferred water-insoluble liquid emollients include fatty acids such as oleic and ricinoleic; fatty alcohols such as oleyl, lauryl and hexadecyl; esters such as diisopropyl adipate, benzoic acid esters of $C_9$–$C_{15}$ alcohols, and isononyl isononanoate; alkanes such as mineral oil; silicones such as dimethylpolysiloxane and cyclic dimethylpolysiloxane; and ethers such as polyoxypropylene butyl ether and polyoxypropylene cetyl ether. Preferred water-insoluble liquid emollients include diisopropyl adipate, 2-ethylhexyl palmitate, dimethylpolysiloxane (50 cst.), and polyoxypropylene (14) butyl ether.

The low melting point wax ingredient of the cosmetic stick product comprises one or more organic compounds which have a melting point in the range between about 35°–82° C.

Suitable types of wax-like compounds include fatty acids, fatty alcohols, fatty acid esters, fatty acid amides, and the like, which have an aliphatic chain length between about 8–30 carbon atoms. Illustrative of wax-like compounds are cetyl alcohol, palmitic acid, myristyl alcohol, stearyl alcohol, paraffin, and the like, and mixtures thereof.

The low melting point wax ingredient can include up to about 30 weight percent, based on the weight of wax ingredient, of a wax which has a melting point between about 82°–105° C. Illustrative of these higher melting waxes are beeswax, spermaceti, carnauba, bayberry, candelilla, montan, ozokerite, ceresin, paraffin, castor wax, Fischer-Tropsch waxes, and the like.

The antiperspirant ingredient typically is a particulate astringent compound which has an average particle size between about 1–100 microns. Superior cosmetic stick properties are obtained if part or all of the antiperspirant ingredient is in the form of particles which have a diameter less than about one micron. Optionally, the antiperspirant ingredient can be precoated with a polymer to prevent interaction with the other cosmetic stick ingredients, and to provide a sustained-release antiperspirant activity under application conditions.

Suitable astringent compounds include aluminum chloride, aluminum chlorohydrate, aluminum sulfocarbolate, aluminum sulfate, aluminum-zirconium chlorohydrate, zinc sulfate, zinc sulfocarbolate, and zirconium chlorohydrate. Preferred types of astringent compounds are aluminum chlorohydrates and aluminum-zirconium chlorohydrates, such as aluminum-zirconium trichlorohydrex glycine. Aluminum-zirconium tetrachlorohydrex glycine is commercially available as Rezal 36 GP Superultrafine (Reheis), and Reach AZP 908 (Reheis).

EXAMPLES

The following Examples are further illustrative of the present invention. The components and specific ingredients are presented as being typical and various modifications can be derived in view of the foregoing disclosure within the scope of the invention.

These Examples demonstrate, by microscopic evaluation of a typical anhydrous deodorant stick formulation, which was enriched in Bisabolol encapsulated according U.S. Pat. No. 5,783,211, that the solid starch based particles survive the manufacturing process and can clearly be detected by visual examination of a thin slice of the semisolid preparation (Example 1).

The Examples further demonstrate that these particles keep their integrity and stay enriched in encapsulated active agent (Example 2 and 3). This is also true even in the case of elevated temperatures like 60° C. This is surprising, since conditions as found in Example 2 and 3 could be considered as good extraction conditions to remove all the active agent from the particle and transfer it to the solvent outside.

In Examples 4 and 5 conditions were applied to the Bisabolol encapsulated product according U.S. Pat. No. 5,783,211 which simulate the triggering activation of water. A full release of the active agent Bisabolol as required was observed.

Example 6 gives a typical lipstick formulation within the concept of the present invention.

Example 7 gives a typical aerosol spray formulation comprising a liposome encapsulated fragrance as biologically active agent.

Example 8 is a perfume extraction test which shows that the perfume oil encapsulating liposomes used in example 7 are tightly encapsulated into the solid matrix of the dry powder composition (Perfume Starchosomes).

Example 1

A water-free antiperspirant stick was formulated according to Table 1. The formulation contains 2% encapsulated fragrance particles (according U.S. Pat..No. 5,783,211).

TABLE 1

| ALUMINIUM ZIRCONIUM STICK ANTIPERSPIRANT | | | |
|---|---|---|---|
| ITEM | % | INGREDIENT | SUPPLIER |
| 1 | 20.00 | Lanette 18 (stearyl alcohol) | Henkel |
| 2 | 2.00 | Cremophor RH 40 (PEG 40 hydrogenated castor oil) | BASF |
| 3 | 0.80 | Cab-O-Sil PTL (silica) | Cabot |

TABLE 1-continued

ALUMINIUM ZIRCONIUM STICK ANTIPERSPIRANT

| ITEM | % | INGREDIENT | SUPPLIER |
|---|---|---|---|
| 4 | 54.70 | Volatile Silicone 7158 (cyclomethicone) | Union Carbide |
| 5 | 2.00 | Kessco EGMS (glycol stearate) | Stepan |
| 6 | 20.00 | AZG-369 powder (aluminum zirconium) | Dow Corning |
| 7 | 0.50 | 2755 lo Micron Talc (talc, 325 mesh) | Whittaker |
| 8 | 2.0 | Encapsulated Fragrance (per U.S. Pat. No. 5,783,211) | DRAGOCO |
| | 100.0 | TOTAL | |

Items 1–5 were added with stirring and heated to 65° C. The batch was clear. Heating was continued to 70° C. and items 6 and 7 were added. Mixing was continuous until the batch was homogeneous. Next, the batch was removed from heat, mixing was continued while cooling to 50° C. Finally, item 8 was added, and the product was poured into molds and allowed to cool down.

The formulation is opaque after cooling. The stick was sliced into thin film samples which were placed on a microscopy slide. With a magnification of 200–400, encapsulated fragrance particles could be identified. The characteristic inside doting of the particles serves as identification of intact particles. Moreover some encapsulated fragrance particles contain an air bubble and break into characteristic parts, which also allows unequivocally identification.

Conclusion

The encapsulated fragrance particles do not dissolve or disappear in the formulation, which would yield a homogeneous distribution of the perfume oil.

Example 2

1,1356 g of encapsulated bisabolol particles (prepared according to U.S. Pat. No. 5,783,211) was added to 10 g of silicone oil (Silicon Fluid 345, Dow Corning Belgium) at 20° C. 110 mg of 2-Ethylhexyl-2-ethylhexenoat (Dragoxat EH, Dragoco) was also added as internal GC-standard. Bisabolol release was followed by GC analysis at 0.25 h, 3 h and 18 h.

Figure 1:
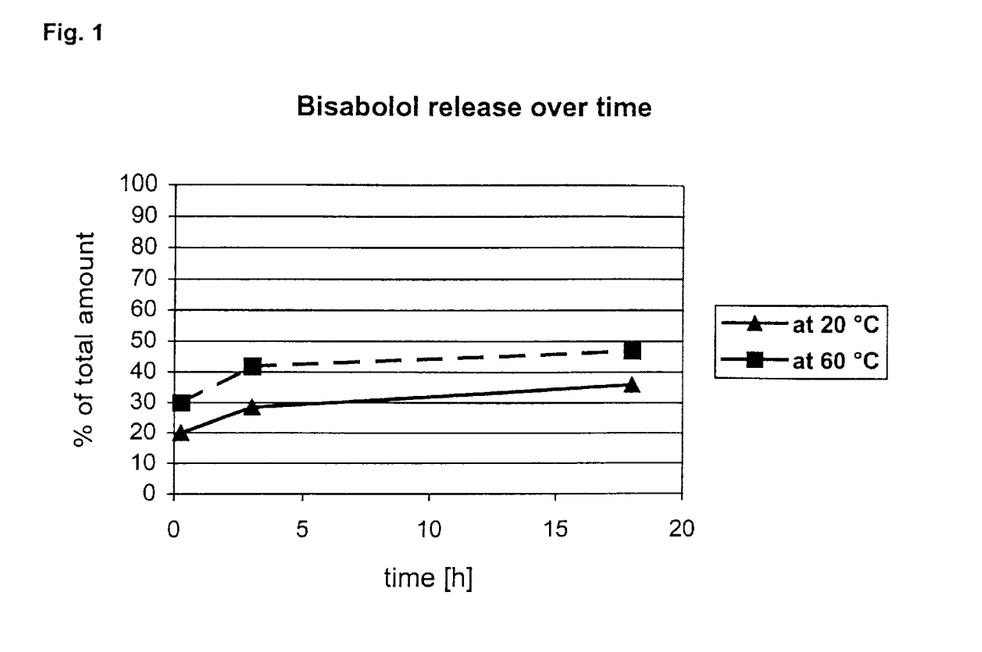
FIG. 1 shows stability of Bisabolol containing particles in silicone oil, product prepared by mixing at 20° C.

The results can be seen in FIG. 1 (triangle marks).

Example 3

1,138 g of encapsulated Bisabolol particles (prepared according to U.S. Pat. No. 5,783,211) was added to 10 g of silicone oil (Silicon Fluid 345, Dow Corning Belgium) at 60° C. 129 mg of 2-Ethylhexyl-2-ethylhexenoat (Dragoxat EH, Dragoco) was also added as internal GC-standard. Bisabolol release was followed by GC analysis at 0.25 h, 3 h and 18 h.

The results can be seen in FIG. 1 (square marks).

Conclusion of Example 2 and 3

The encapsulation technique according to U.S. Pat. No. 5,783,211 yields particles which keep up an increased concentration of active agent over a period of time even at 60° C.

Example 4

Figure 2:
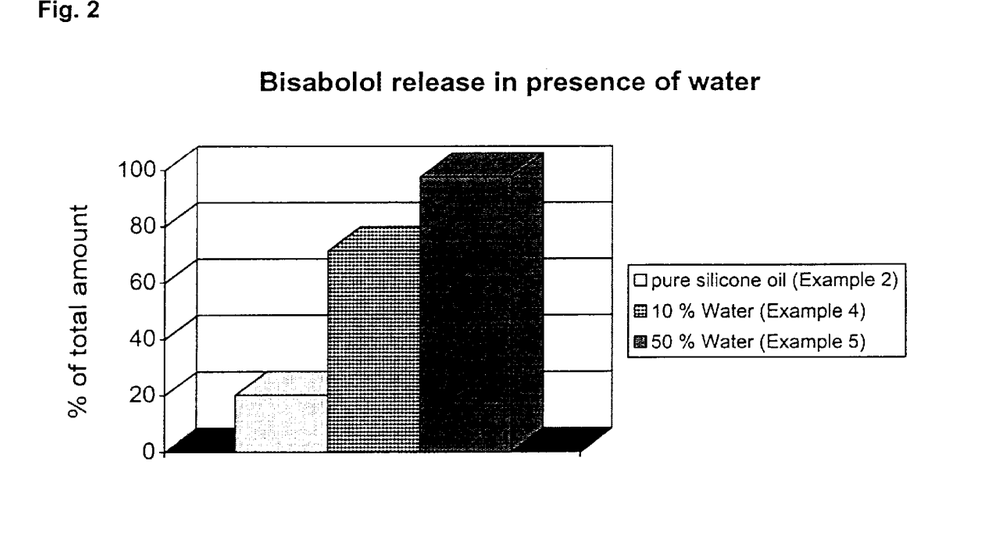
FIG. 2 shows stability of Bisabolol containing particles in silicone oil, product prepared by mixing at 60° C.

1.0136 g of encapsulated Bisabolol particles (prepared according to U.S. Pat. No. 5,783,211) were added to 10 g of silicon oil (Silicone Fluid 345, Dow Corning Belgium) at 20° C. 0.4046 g of 2-Ethylhexyl-2-ethylhexenoat (Dragoxat EH, Dragoco) were also added as internal GC-standard. Finally 1 g of water was added. Bisabolol release was followed by GC analysis of the organic phase after 15 minutes. Results can be seen in FIG. 2.

Example 5

1.2895 g of encapsulated Bisabolol particles (prepared according to U.S. Pat. No. 5,783,211) were added to 15 g of silicon oil (Silicone Fluid 345, Dow Corning Belgium) at 20° C. 0.4356 g of 2-Ethylhexyl-2-ethylhexenoat (Dragoxat EH, Dragoco) were also added as internal GC-standard. Finally 10 g of water was added. Bisabolol release was followed by GC analysis of the organic phase after 15 minutes. Results can be seen in FIG. 2.

Conclusion of Examples 4 and 5

In presence of water a quick release of Bisabolol could be observed. In case of a skin application a peak delivery of Bisabolol will be the consequence if water enters the treated skin side.

Example 6

A lipstick is formed comprising the following ingredients in the following amounts:

| % | Ingredient | Supplier |
|---|---|---|
| 5.00 | Cetyl Acetate Candy Acetylated Lanolin Alcohol (Acetulan) | Amerchol |
| 5.00 | PEG-2 Lanolin Alcohol Ether (Solulan PB 2) | Amerchol |
| 23.00 | Isopropyl Palmitate (Lexol IPP) | Inolex |
| 1.00 | Silica (Cab-O-Sil HS5) | Presperse |
| 10.00 | Pigments | Clark Colors |
| 6.00 | Beeswax USP | Ross |
| 7.00 | Candelilla Wax | Ross |
| 5.00 | Ozokerite Wax | Ross |
| 3.00 | Carnuba Wax | Ross |
| 5.00 | Myristyl Lactate (Ceraphyl 50) | Van Dyk |
| 27.80 | Castor Oil (Em Con Co.) | Fanning |
| 0.10 | Methylparaben | Costec |
| 0.10 | Propyl Paraben (Cosept P) | Costec |
| 2.00 | Starchosomes | Dragoco |
| 100.00 | TOTAL | |

The pigments were ground in a blend of Acetulan, Solulan PB2 and isopropyl palmitate. The remaining ingredients other than Starchosomes® were heated to 85–90° C. until uniform and free of air. Next, the pigment concentrate was added and slow mixing was continued at 85–90° C. until the mixture was uniform and free of air. The mixture was cooled to 65° C. and Starchosomes® were added with proper mixing. The final product contained Dragosantol as active agent encapsulated within liposomes, which liposomes were imbedded in a starch matrix to form particles, which particles were homogeneously dispersed in an anhydrous lipophilic solid organic matrix. The lipstick, when applied, provided antiphlogistic properties over an extended period of time.

Example 7

Preparation of an Aerosol spray formulation for the delivery of Perfume Starchosomes (i.e. a spray dried powder composition comprising active agent encapsulating liposomes) to human skin:

Step 1: Preparation of Liposome Dispersion (Nanoparticle Dispersion)

57 g Soy Lecithin (Nat 8539, Rhone Poulenc, Nattermann), 2.2 g Potassium Cetyl Phosphate (Amphisol K, Givaudan), 0.8 g Vitamin E, 7 g Water and 330 g of Perfume oil (the formulation of which is given below) is mixed at 50° C. to yield a lipid mixture. This lipid mixture is dispersed into 770 g water by high shear force mixing. The resulting white dispersion is then further processed by homogenizing with a high pressure-homogenizing unit (Rannie, Model Mini Lab, Type 8.30H) in a first step at 800 bar and in a successive second step at 100 bar. In total 1167 g of dispersion is yielded having a mean particle size between 180 and 250 nm, according to photon correlation spectroscopy (using a Coulter to particle sizer).

| Formulation of perfume oil: | |
|---|---|
| 10-Undecenal | 0.5% |
| Bergamot oil | 5.4% |
| Dihydromyrcenol | 27.4% |
| Eugenol | 1.8% |
| Habanolide | 7.2% |
| Helional** | 1.8% |
| Hexylcinnamonic acid | 10.9% |
| Linalylacetate | 8.9% |
| Menthol | 2.7% |
| Orange oil | 26.8% |
| Ortho-Ylanate*** | 3.6% |
| Ysamber K*** | 3.6% |

*tradename used by Firmenich
**tradename used by IFF
***tradename used by Dragoco
****ortho-tert.-butyl-cyclohexylacetate Step 2: Preparation of an Aqueous Mixture of Active Agent Encapsulating Liposomes, Starch and a Hydrocolloid Gum 264 g water and 258 g of octylsuccinylated Corn starch (hydrocolloid gum; Capsul E, National Starch) is mixed with 800 g Liposome dispersion of step 1. To the resulting dispersion 258 g solid Maltodextrin (degraded Wheat starch, 20% Glucose equivalents; Roquette, Frankfurt) is added slowly. After stirring the resulting viscous mixture for 5 minutes the pH is adjusted with Sodium hydroxide solution to pH=5. The resulting aqueous mixture contains a dry matter content of approximately 50% by weight.

Step 3: Preparation of a Spray Dried Powder Composition

The aqueous mixture of step 2 is spray dried by introducing it into a spray drying tower operated at 200° C. and at a feed rate allowing an exit temperature of 75° C. The procedure yielded 721 g of an off-white powder. Sauter mean particle size is 35 μm, 90% of particles are below 65 μm (measured with a Malvern particle sizer).

Step 4: Preparation of the Aerosol Spray Formulation

For the preparation of 100 g Aerosol spray formulation 1.5 g of the spray dried powder composition ("Perfume Starchosomes") is placed in a pressure-proof aerosol can (sprayer) together with 5.0 g Cyclomethicone (Dow Corning 344 Fluid), 5.0 g volatile Silicone (Wacker-Belsil DM 0.65). 88.5 g Isobutane/Propane blend (Propellant A-46 blend, Aeropres) are added to disperse and pressurize the mixture.

The resulting Aerosol spray formulation upon shaking the sprayer allows an easy application of the solid Perfume Starchosomes onto the skin.

| Formulation according to step 4: | |
|---|---|
| Perfume Starchosomes according to step 3 | 1.5% |
| Cyclomethicone (Dow Corning 344 Fluid) | 5.0% |
| Volatile Silicone (Wacker-Belsil DM 0.65) | 5.0% |
| Isobutane/Propane blend (Propellant A-46 blend, Aeropres) | 88.5% |

Example 8

Perfume Extraction Test of Perfume Starchosomes of Example 7:

50 g of Perfume Starchosomes prepared according to example 7, step 3 were extracted by using 200 g of distilled Pentan. The Pentan extract is removed by filtering and collected. The extraction procedure is repeated two times. The combined extracts have then been concentrated by careful evaporation of the Pentan at 20° C. and application of vacuum. The remaining residue was weighed and yielded 0.23 g of an oily residue. Based on perfume content this represents an extract yield of only 1.6% based on the total amount of perfume oil.

This shows that the Perfume Oil encapsulating liposomes are tightly encapsulated into the solid matrix of the Perfume Starchosomes.

Although this invention has been described in its preferred form with a certain degree of particularity with respect to starch encapsulated Bisabolol and starch encapsulated perfume, it is understood that the present disclosure of the preferred form has been made only by way of example and that numerous changes in the details of structures and the composition of the combination may be resorted to without departing from the spirit and scope of the invention.

What is claimed is:

1. A cosmetic or pharmaceutical product comprising:

an anhydrous solid or liquid dispersion medium, and about 0.01–20 weight percent, based upon the total weight of said product, of solid particles dispersed in said anhydrous dispersion medium, said solid particles comprising a) (i) at least one of octylsuccinylated starch and (ii) enzymatic modified starch, b) liposomes encapsulating a biologically active agent, and, optionally, c) a hydrocolloid gum.

2. A cosmetic or pharmaceutical product according to claim 1, wherein said liposomes have a size of from 100 to 1000 nm.

3. A cosmetic or pharmaceutical product according to claim 1, wherein said dispersion medium is a lipophilic organic matrix comprising 10–55 wt. % volatile oil, 1–35 wt. % liquid emollient, and 12–30 wt. % wax having a melting point between about 35°–82° C.

4. Cosmetic or pharmaceutical product according to claim 3, wherein said volatile oil ingredient is selected from silicone and branched-chain hydrocarbon compounds.

5. Cosmetic or pharmaceutical product according to claim 4, wherein said volatile oil is a cyclic or linear polydimethylsiloxane containing between 3–9 silicon atoms or a linear polydimethylsiloxane illustrated by the formula:

$$(CH_3)_3Si—O[Si(CH_3)_2—O]_n—Si(CH_3)_3$$

where n is an integer with a value of about 1–7.

6. Cosmetic or pharmaceutical product according to claim 4, wherein the volatile oil ingredient comprises a $C_{12}$–$C_{20}$ branched-chain hydrocarbon.

7. Cosmetic or pharmaceutical product according to claim 3, wherein the liquid emollient ingredient is a water-insoluble organic acid, ester or ether compound.

8. A cosmetic or pharmaceutical product according to claim 3, wherein the wax is selected from the group consisting of fatty alcohols, fatty acids, fatty acid esters and fatty acid amides.

9. Cosmetic or pharmaceutical product according to claim 1, wherein said hydrocolloid gum is selected from the group consisting of xanthan, maltodextrin, galactomanan and tragacanth.

10. Cosmetic or pharmaceutical product according to claim 1, wherein said biologically active agent encapsulated in said liposomes is selected from the group consisting of anti-inflammatory, antiphlogistic, antibacterial, anti-perspirant, astringent, and anti-fungal agents.

11. A cosmetic or pharmaceutical product formed by a process comprising (a) incorporating a biologically active agent into liposomes (b) forming an aqueous mixture of active agent encapsulating liposomes, starch and, optionally, a hydrocolloid gum, (c) spray drying said mixture to form a dry powder composition, (d) dispersing said dry powder composition into an anhydrous dispersion medium.

12. A solid cosmetic or pharmaceutical product formed by a process comprising (a) incorporating a biologically active agent into liposomes (b) forming an aqueous mixture of active agent encapsulating liposomes, starch and, optionally, a hydrocolloid gum, (c) spray drying said mixture to form a dry powder composition, (d) dispersing said dry powder composition into an anhydrous solid lipophilic cosmetic matrix, and (e) shaping the product of step (d).

13. A cosmetic or pharmaceutical aerosol spray formulation formed by a process comprising (a) incorporating a biologically active agent into liposomes (b) forming an aqueous mixture of active agent encapsulating liposomes, starch and, optionally, a hydrocolloid gum, (c) spray drying said mixture to form a dry powder composition, (d) dispersing said dry powder composition into an anhydrous liquid dispersion medium.

14. An essentially anhydrous cosmetic or pharmaceutical product comprising:

a lipophilic, anhydrous dispersion medium, and about 0.01–20 weight percent, based upon the total weight of said product, of particles homogeneously dispersed in said dispersion medium, said particles comprising liposome microcapsules containing active agent incorporated in a particle forming matrix of a water absorbent component.

15. Cosmetic or pharmaceutical product according to claim 1, wherein said liposomes have a size of from 100 to 300 nm.

* * * * *